United States Patent [19]

Dalling et al.

[11] Patent Number: 5,425,715
[45] Date of Patent: Jun. 20, 1995

[54] RELOADABLE INJECTOR

[75] Inventors: N. Lawrence Dalling, Cross Junction, Va.; William R. Pearson, Laurel, Md.

[73] Assignee: Survival Technology, Inc., Rockville, Md.

[21] Appl. No.: 102,257

[22] Filed: Aug. 5, 1993

[51] Int. Cl.6 ............................................. A61M 5/20
[52] U.S. Cl. ................................. 604/136; 604/135; 604/157
[58] Field of Search ............... 604/131, 134, 135, 136, 604/142, 148, 157, 156, 192, 197

[56] References Cited

U.S. PATENT DOCUMENTS

| | | |
|---|---|---|
| 2,752,918 | 7/1956 | Uytenbogaart . |
| 3,403,679 | 10/1968 | Sinclair . |
| 3,797,489 | 3/1974 | Sarnoff .................. 604/136 |
| 4,484,910 | 11/1984 | Sarnoff . |
| 4,518,384 | 5/1985 | Tarello . |
| 4,529,403 | 7/1985 | Kamstra . |
| 5,026,349 | 6/1991 | Schmitz et al. ......... 604/135 |
| 5,085,642 | 2/1992 | Sarnoff et al. .......... 604/135 |
| 5,104,380 | 4/1992 | Holman et al. ......... 604/157 |
| 5,137,516 | 8/1992 | Rand . |
| 5,167,632 | 12/1992 | Eid et al. ............... 604/136 |
| 5,176,643 | 1/1993 | Kramer et al. .......... 604/135 |

*Primary Examiner*—John G. Weiss
*Attorney, Agent, or Firm*—Cushman Darby & Cushman

[57] ABSTRACT

A reloadable automatic injector comprises a reusable power pack assembly for effectuating multiple injection operations. The power pack assembly includes an outer body and an energy releasing assembly disposed within the body. The energy releasing assembly is capable of providing multiple energy releasing strokes. A disposable cartridge assembly is provided which is engageable with the power pack assembly and forms an elongate injection assembly therewith. The cartridge assembly is adapted to receive energy from the power pack during one of the energy releasing strokes. The cartridge assembly includes a housing in which a charge of medicament and a needle is contained. A plunger is disposed within the housing for forcing the medicament through the needle. The cartridge assembly receives energy from the power pack assembly during one of the energy releasing strokes to enable the needle to project from the protected position to an unprotected projecting position from the housing and to enable the plunger to force the medicament through the needle. In addition, a needle return spring is provided for returning the needle from the unprotected position to the protected position within the housing so that the housing provides the needle with a rigid protective outer covering for sanitary disposal of the cartridge assembly.

14 Claims, 3 Drawing Sheets

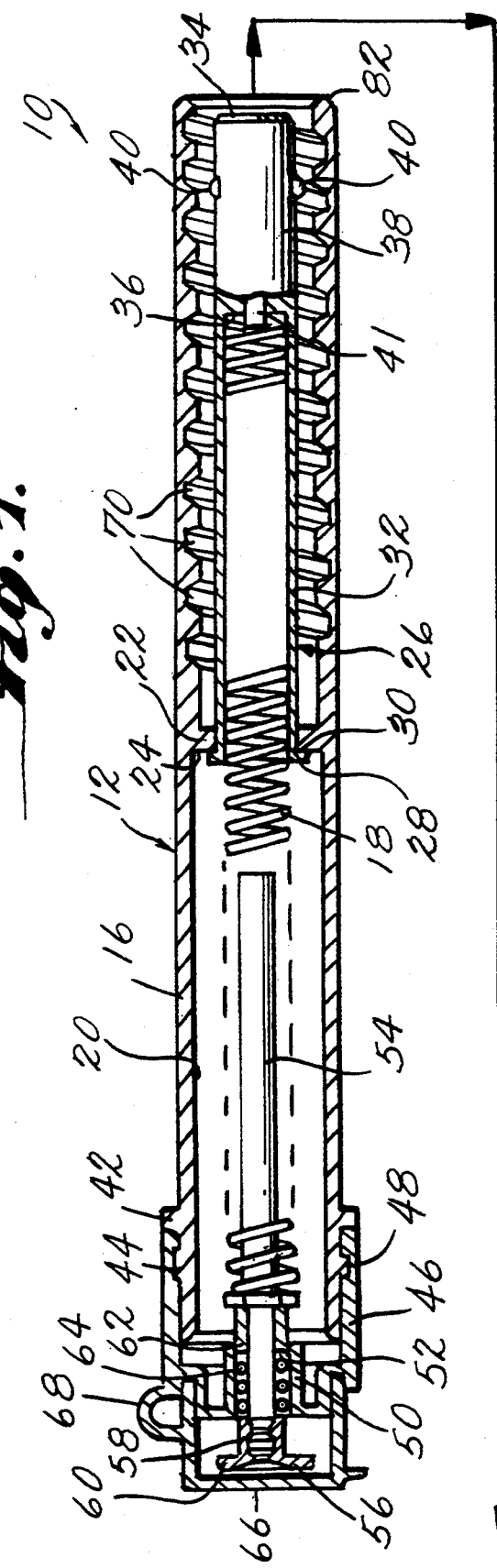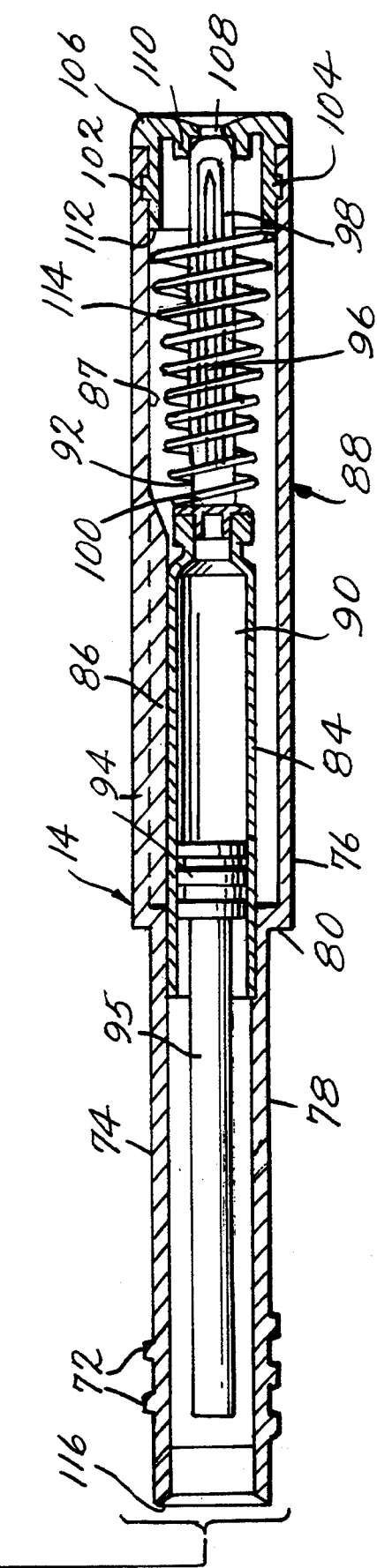
Fig. 1.

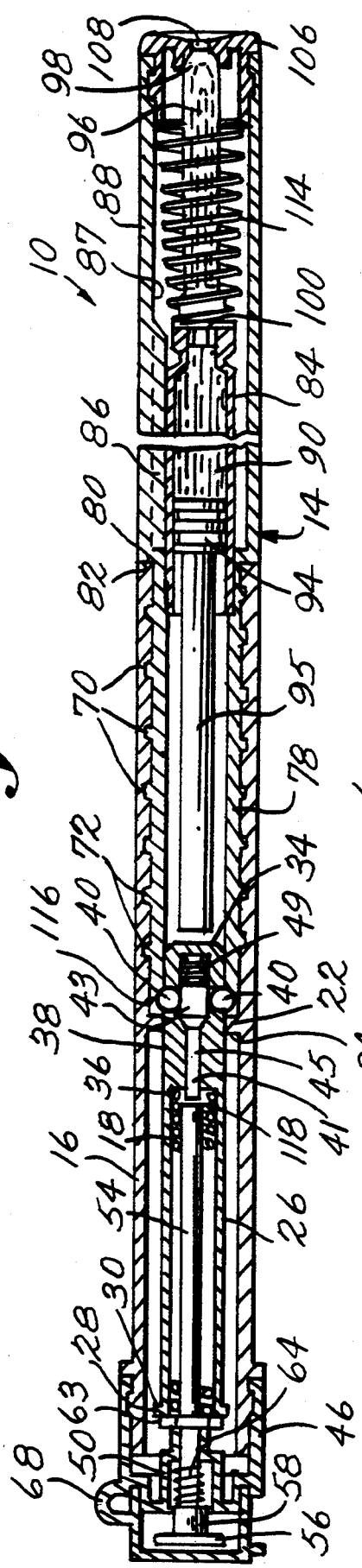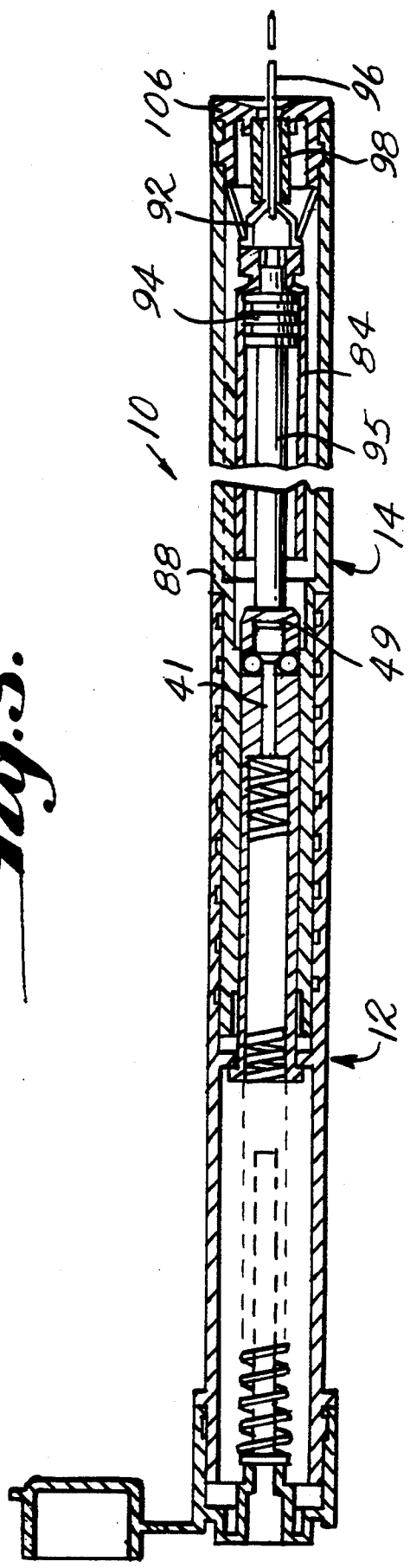

000
RELOADABLE INJECTOR

BACKGROUND OF THE INVENTION

1. Field of the Invention

This invention relates to an apparatus for injecting medicaments and to improvements in apparatus suitable for effecting multiple injections.

Automatic injectors are well known. Basically, an automatic injector is a device for enabling an individual to self-administer a dosage of a liquid medicament. An advantage of automatic injectors is that they contain a measured dosage of a liquid medicament in a sealed, sterile condition capable of storage in such condition for an extensive period of non-use, during which period immediate injection of the stored dosage may be accomplished at any time under the most severe emergency conditions. Another advantage of automatic injectors is that the administration of the self-contained dosage of liquid medicament is accomplished without the necessity of the user initially seeing the hypodermic needle through which the medicament is injected or of manually penetrating such a visible needle into the user's own tissue. Instead, an automatic injector includes a releasable stressed spring assembly. This assembly includes a stressed spring, a releasable mechanism for releasably retaining the spring in a stressed storage position and a releasing mechanism for releasing the releasable mechanism in response to a predetermined actuating procedure.

Automatic injectors have heretofore been particularly suited for use under emergency situations. For example, many tens of millions of such automatic injectors have been manufactured and sold containing nerve gas antidotes for use under emergency chemical warfare conditions. Typical units which have been utilized for this purpose are disclosed in U.S. Pat. Nos. 2,832,339, 3,882,863, and U.S. Pat. No. 4,031,893. In addition, units of this type have been proposed for use in administering antiarrhythmic medicaments under emergency conditions relating to heart attack medical situations. Such use has been in conjunction with portable monitors as is evident from the disclosure contained in U.S. Pat. Nos. 3,910,260 and 4,004,577. It has also been proposed to provide other medicaments useful in treating heart attack symptoms, such as clot selective thrombolytic agents (e.g., tPA) and related medicaments. Finally, automatic injectors have been marketed in recent years containing a dosage of epinephrine as an antidote for counteracting severe allergic reactions, as for example, bee stings and the like.

In all of these instances, the emergency use aspect of the automatic injectors is of primary significance.

SUMMARY OF THE INVENTION

The present invention stems from the recognition that the advantages of automatic injectors are not limited only to emergency situations, but that there are many other medicinal administration situations requiring a much more frequent usage where the painlessness and simplicity of actuation of an automatic injector combined with other conveniences, would be sufficiently desirable to many individuals to warrant the added costs in comparison to the more simple and less costly manual syringes in widespread use. For example, recently the drug erythropoietin has been approved by the FDA in combating anemia. The drug is particularly useful to kidney patients, AIDS patients, and patients donating blood for their own use in anticipation of elective surgery. Such patients may have need for the administration of erythropoietin as frequently as once a week. An automatic injector provides a very convenient way of allowing the patient to administer the necessary erythropoietin without requiring the patient to become proficient in inserting a needle into his own flesh. Under circumstances of this type, it is desirable to provide the user with maximum convenience in availability, handling and use of the automatic injector, while doing so by the least expensive means possible.

To accomplish this objective, there have been a number of automatic injectors which provide a reusable power pack to effectuate an injection of a medicament containing cartridge. By providing such a reloadable power pack, the user is able to save expenses in that the same firing mechanism can be used several times rather than being discarded after each injection. Such a reusable power pack has been disclosed in U.S. Pat. No. 2,752,918. However, in this patent, the injection needle formulates part of the power pack assembly, and must therefore be cleaned after each and every use to prevent contamination thereof. In U.S. Pat. No. 3,403,679, there is proposed an automatic injector which provides a reloadable injector which is capable of reloading a medicament cartridge containing a charge of medicament and a needle disposed therein. The problem associated with this type of injector is that after an injection, an exposed needle must be discarded before replacing a fresh cartridge within the power pack. Such exposed needles often contain traces of blood, which may become the source of transmittable disease. Therefore, great care and expense must be taken when the cartridge of such an injector is disposed. The same sort of problem is presented in our earlier U.S. Pat. No. 4,518,384. In that patent, there is disclosed several embodiments of a reloadable firing mechanism which is cooperable with an expendable medicament containing clip. The clip disclosed in this patent contains several medicament/needle cartridges which are successively ejected from the clip housing after each injection. In those cartridges, the needle must be discarded without the benefit of an outer rigid protective housing to prevent an unwary individual from accidently pricking himself with the expended needle. In addition, this device is rather bulky and is not suited for a user to carry on his or her person, for example in the individual's pocket.

In U.S. Pat. No. 5,137,516, there is also disclosed a reloadable injector. However, as disclosed in that patent, after an injection operation, the needle is left in an extended position, and it is necessary to place an endcap over the exposed needle to cover the same before disposal. Since the user must bring the endcap towards the needle and place it thereover, the user risks self-pricking when covering the needle. In another embodiment of this patent, the user must place the exposed needle into a relatively large and expensive compartment while the needle is still secured to the power pack assembly. Additionally, in both of the aforementioned embodiments, the outer covering is separately provided rather than integrally formed with the injector and may be lost or misplaced during an injection procedure.

It is an object of the present invention to resolve the problems stated above. This object is accomplished by providing a reloadable, automatic injector comprising a reusable power pack assembly for effectuating multiple injection operations. The power pack assembly includes an outer body and an energy releasing assembly disposed within the body. The energy releasing assembly is capable of providing multiple energy releasing strokes. A disposable cartridge assembly is provided which is engageable with the power pack assembly and forms an elongate injection assembly therewith. The cartridge assembly is adapted to receive energy from the power pack during one of the energy releasing strokes. A charge of medicament is disposed within the housing, and a needle is held in a normally protected position within the housing. A plunger is disposed within the housing for forcing the medicament through the needle. The cartridge assembly receives energy from the power pack assembly during one of the energy releasing strokes to enable the needle to project form the protected position to an unprotected projecting position from the housing and to enable the plunger to force the medicament through the needle. In addition, a needle return means is provided for returning the needle from the unprotected position to the protected position within the housing so that the housing provides the needle with a rigid protective outer covering for sanitary disposal of the cartridge assembly.

It is another object of the present invention to provide a disposable cartridge for a reloadable automatic injector assembly comprising a rigid housing which is adapted to be engaged with a power pack assembly capable of effectuating an injection. A single charge of medicament and a needle are both contained within the housing. In addition, a plunger is disposed within the housing for forcing the medicament through the needle. The cartridge assembly is adapted to receive an energy releasing stroke from the power pack assembly to enable the needle to project from the protected position to an unprotected projecting position from the housing and to enable the plunger to force the medicament through the needle. In addition, a needle return spring is provided in order to return the needle to the protected position within the housing from the unprotected projecting position so that the housing provides the needle with a rigid protective outer cover for sanitary disposal of the cartridge.

It can be seen that the present invention allows a needle containing cartridge to be disengaged from a power pack assembly after an injection operation. The needle return spring within the cartridge assembly automatically returns the needle into the rigid outer housing of the cartridge so that the cartridge provides a self-contained protective covering for the used needle. Upon disposal, there is no chance of an unwary individual to accidently prick himself with the used needle. In addition, the needle return spring allows the needle to be protected without the need for an auxiliary cap to be placed thereover. Thus, there is no cap to be lost and there is no manual movement of a cap towards an exposed needle to cover the same. Finally, it can be appreciated that the narrow elongate shape of the injection assembly allows the device to be easily transported by the user.

These and other objects of the present invention will become more apparent during the course of the following detailed description and appended claims. The invention may be best understood with reference to the accompanying drawings wherein illustrative embodiments are shown.

BRIEF DESCRIPTION OF THE DRAWINGS

FIG. 1 is a longitudinal sectional view of one embodiment of an automatic injector, embodying the principles of the present invention, which shows a power pack and cartridge assembly disengaged from one another.

FIG. 2 is a longitudinal sectional view of the embodiment of FIG. 1 after the power pack and cartridge assembly have been engaged with one another.

FIG. 3 is a longitudinal sectional view of the embodiment of FIGS. 1 and 2 after the injector has been activated.

DETAILED DESCRIPTION OF THE DRAWINGS

Figure 4:
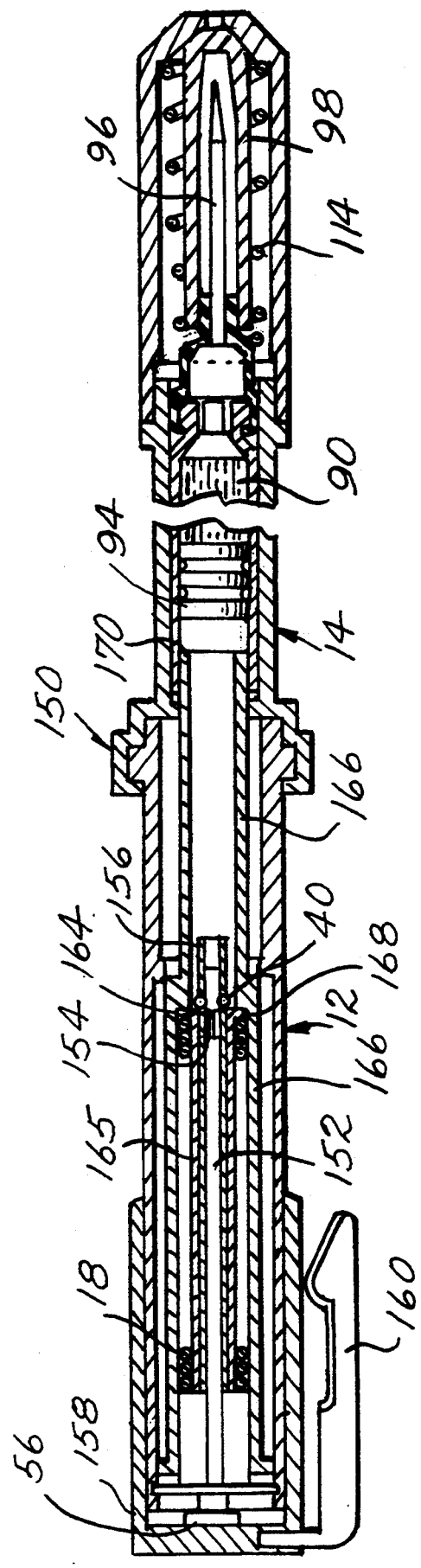
FIG. 4 is a longitudinal sectional view of a second embodiment of an automatic injector embodying the principles of the present invention.

Turning now to FIG. 1, there is shown a reloadable automatic injector generally indicated at 10. The injector includes a power pack assembly 12 and a cartridge assembly 14.

The power pack assembly 12 is reusable in that it may be repeatedly cocked and fired to provide multiple energy releasing strokes and is successively engageable with a number of cartridge assemblies 14 to effectuate the same number of injection operations on which a medicament is injected into the flesh of a patient.

Power pack assembly 12 has a body 16 and an energy releasing assembly disposed therein. The energy releasing assembly includes a power spring 18, which can be compressed and then released to provide energy for the energy releasing strokes.

Body 16 is substantially in tubular form, and has an inner surface 20. At about the midpoint of tubular body 16, an annular ring portion 22 extends inwardly toward a longitudinal axis of body 16 from inner surface 20. Annular ring portion 22 divides the body into forward and rearward portions and has a rearwardly facing surface 24.

Disposed within body 16 is a concentrically disposed release pin assembly 26. Release pin assembly 26 has a substantially tubular shape and has an outer surface which is held in a slidable relation with a surface comprising the inner peripheral circumference of annular ring portion 22. Release pin assembly 26 has an outwardly extending annular portion 28 which has a slightly greater diameter at the rearward end thereof. Annular portion 28 has a forwardly facing surface 30 which is engageable with the rearwardly facing surface 24 of annular ring portion 22 to limit the forward movement of release pin assembly 26 with respect to body 16.

While the greater portion of release pin assembly 26 comprises a tubular sleeve-like portion 32, the forward portion 38 of the release pin assembly has a substantially cylindrical shape with forward and rearward circular ends 34 and 36, respectively.

Forward portion 38 of release pin assembly 26 has at its outer periphery release pin balls 40 protruding radially outwardly therefrom. The release pin balls are substantially spherical in form, but have only a portion thereof protruding from the forward portion 38. The balls 40 are held in protruding relation by a central pin 41, as best seen in FIG. 2, disposed within forward portion 38. Central pin 41 has a large diameter portion 43 and a narrowed diameter portion 45. The exterior surface of the large diameter portion 43 is normally in engagement with balls 40 so as to keep them protruding from forward portion 38. Central pin 41 is forwardly moveable against the biasing action of coil spring 49, by operation of operating rod 54, so that narrowed diameter portion 45 is in radial alignment with balls 40 so as to allow balls 40 to move inwardly into forward portion 38.

Pin 41 has a rearward end thereof extending from the circular end 36 of forward portion 38 rearwardly into sleeve-like member 32 towards the rearward end of power pack assembly 12.

Referring back to FIG. 1, it can be seen that body 16 has a forward annular ridge 42 formed on the exterior periphery thereof in rearwardly spaced relation to the forward end thereof and a rearward ridge 44 of sightly lesser exterior diameter disposed in rearwardly spaced relation with respect to the forward ridge 42. A rearward end portion 46 has a somewhat tube-like shape which is adapted to receive therein the rearward portion of body 16. End portion 46 has along its interior periphery an annular groove 48 which is adapted to receive rearward annular ridge 44, which allows end portion 46 to be retained at the rearward end of body 16.

End portion 46 has a central recessed portion 50 with a central hole 52 therethrough. Hole 52 provides a passage for an operating rod 54, which extends from an exterior position of end portion 46 through hole 52 and into the inner confines of power spring 18 at the rearward end thereof.

The rearward end of operating rod 54, which extends rearwardly from end portion 46, is provided with a manually engageable pushbutton 56 having a narrow forward portion 58 which can be received into recessed portion 50 of end portion 46, and a rearward portion 60 having an enlarged diameter which cannot be received into recessed portion 50.

Recessed portion 50 has an annular inturned portion 62 which forwardly provides a seat for thrust washer 63 and rearwardly provides a forward seat for a compression spring member 64 which biases pushbutton 56 outwardly away from end portion 46.

As shown, a flip-top cap 66 is provided to cover pushbutton 56 so as to prevent an accidental actuation of the unit. Flexible hinge element 68 is provided to allow flip-top cap 66 to pivot with respect to end portion 46.

At the forward portion of power pack assembly 12, inner surface 20 is provided with receiving threads 70 which are capable of receiving threads 72 disposed on the exterior surface 74 of tubular cartridge assembly 14, which will now be described in greater detail.

While cartridge assembly 14 is of a substantially tubular shape, the forward portion 76 thereof has a slightly greater diameter than the rearward portion 78 thereof. At the transition between the rearward and forward portions 78 and 76, respectively, there is a rearwardly facing annular surface 80, which is adapted to engage the forward annular surface 82 of body 16 when the cartridge assembly 14 is secured to power pack assembly 12.

Disposed within cartridge assembly 14 is a container or cartridge 84 which is held in a slidable relation with equally spaced interior ribs 86 formed on the inner surface 87 of a rigid housing generally indicated at 88. Cartridge 84 is preferably made of glass, and contains a liquid medicament 90 therein. The cartridge 84 is open at its rearward end and necked down at its forward end to receive a hub assembly 92. A plunger 94 closes the open rearward end of the cartridge 84 and is mounted therein for forward sliding movement in sealed relation with the interior of the cartridge 84. Plunger 94 has an elongate plunger rod 95 extending in a rearward direction therefrom. The function of plunger rod 95 will be described in conjunction with FIGS. 2 and 3. The hub assembly 92 has fixed to the forward end thereof the rearward end of a hypodermic needle 96 which extends forwardly therefrom. The hypodermic needle 96 is incased with a resilient sheath 98 which extends forwardly from the crimped forward portion of hub assembly 92. Preferably, as shown, the hub assembly 92 is of the type which includes a burstable seal 100 in the rearward portion thereof, such as disclosed in U.S. Pat. Nos. 3,380,449 and 3,391,695, the disclosures of which are hereby incorporated by reference into the present specification. The seal 100 of the hub assembly 92 serves to sealingly confine the liquid medicament 90 within the cartridge 84 at its forward end, with the plunger 94 confining it at its rearward end.

The forward end of rigid housing 88 is provided with an annular groove 102 which is adapted to receive an annular ridge 104 of a forward cap member 106. Cap member 106 has a central hole 108 which is large enough to permit needle 96 to project therethrough while small enough to prevent sheath 98 from doing the same. An annular guide 110 surrounds hole 108 and bears against sheath 98 and operates to maintain needle 96 in alignment with hole 108. Cap member 106 has a flat annular surface 112 at its innermost extremity with respect to housing 88. Surface 112 provides a bearing surface for a return spring 114 which is disposed between surface 112 and a portion of hub assembly 92. In FIG. 1, all three springs 64, 18, and 114 are shown in a relaxed condition.

In FIG. 2, there is shown the reloadable automatic injector 10 in assembled condition wherein the cartridge assembly 14 is engaged with power pack assembly 12. As described above, this engagement is accomplished by cooperably screwing threads 72 of tubular cartridge 14 in a clockwise direction with respect to threads 70 of power pack assembly 12.

As the two assemblies 12 and 14 are screwed together, a leading surface 116 of cartridge assembly 14 is biased against the release pin balls 40 so as to move the entire release pin assembly rearwardly therewith. As the release pin assembly 26 is moved rearwardly, power spring 18 is compressed between circular end 36 of forward portion 38 and a forwardly facing surface of thrust washer 63.

Cartridge assembly 14 is continuously screwed into power pack assembly 12 until the annular surface 80 of the cartridge assembly 14 meets the forward annular surface 82 of power pack assembly 12 which prevents further screwing. When the screwing action is complete, balls 40 are left only a slight distance from annular ring portion 22 of body 16, and the forward end 118 of operating rod 54 is left only a slight distance from the rearward end of central pin 41, which extends rearwardly from circular end 36. It can be appreciated that the screwing action operates to cock or reload the power spring 18 to prepare it for an energy releasing stroke.

The actuation of the reloadable automatic injector 10 is described in conjunction with FIGS. 2 and 3. There, it can be seen that before the injector can be actuated, flip-top cap must be pivoted on hinge 68 to permit access to activating pushbutton 56. When exposed, pushbutton 56 may be manually engaged and moved forward so that the forward end 118 of operating rod 54 comes into contact with the rearward end of pin 41.

It can be seen that, as pushbutton 56 is moved inwardly toward body 16, the narrow portion 58 is permitted to enter recess 50 of end portion 46 as compression spring member 64 is compressed therebetween. It can be appreciated that pushbutton 56 may be pressed only a slight distance before compression spring member 64 becomes fully compressed such that pushbutton 56 can no longer move forward. However, the slight distance which operating rod 54 is moved forwardly within power pack assembly 12 is enough for it to engage and move pin 41 forwardly so that release pin balls 40 can ride into narrowed diameter portion 45 of pin 41. As a result, the balls 40 can ride over leading surface 116 of cartridge assembly 14. Once the outer periphery of release pin balls 40 become flush with the exterior surface of forward portion 38, the release pin assembly 26 becomes free to slidably move within rearward portion 78 of cartridge assembly 14 towards the forward end of the injector.

As release pin assembly 26 is accelerated towards the forward end of the reloadable automatic injector 10 by power spring 18, the forward circular end 34 thereof is forced against the rearward end of plunger rod 95. This action, in turn, forces the entire cartridge 84 towards the forward cap member 106. This, in turn, causes spring 114 to become compressed, as needle 96 pierces through sheath 98 and the needle exits the rigid housing through the hole 108 in cap member 106. In this forward motion of the cartridge and needle, the sheath 98 and spring 114 operate as shock absorbers to prevent breakage of glass cartridge 84.

After cartridge 84 reaches its forwardmost position in rigid housing 88, the release pin assembly 26 continues its forward motion so that forward circular end 34 biases plunger rod 95 and plunger 94 forwardly with respect to cartridge 84, thereby compressing medicament 90 to the extent that burstable seal 100 is ruptured and medicament is permitted to enter the rearward end and through needle 96 to be injected into a patient.

The forwardly facing surface 30 of annular portion 28 of release pin assembly 26 finally reaches the rearwardly facing surface 24 of annular ring portion 22, which stops further forward motion of release pin assembly 26.

As shown in FIG. 3, the needle 96 is held in an extended position after an injection operation. After such operation, the entire reloadable injector 10 is moved away from the patient so that the needle is withdrawn from the flesh of the patient.

The disengagement of cartridge assembly 14 from power pack assembly 12 will now be described. Simply, cartridge assembly 14 is rotated in a counterclockwise direction with respect to power pack assembly 12 until it is completely disengaged therefrom. As the cartridge assembly 14 is unscrewed from power pack assembly 12, the spring 114 urges cartridge 84 away from cap member 106 to thereby return needle 96 into rigid housing 88. After complete disengagement, the power pack assembly is substantially in the same condition as shown in FIG. 1 and is ready to receive a new cartridge assembly. Coil spring 49 urges central pin 41 rearwardly so that large diameter portion 43 is once again aligned with balls 40, which once again project from forward portion 38.

The used cartridge assembly 14, on the other hand, ends up in substantially the same condition as shown in FIG. 1, with the exception of the fact that plunger 94 and plunger rod 95 are forwardly disposed relative to the cartridge 84, and medicament 90 is no longer contained within the cartridge. However, as shown in FIG. 1, the needle is held in a sheathed position within rigid housing 88 and can be readily disposed without the possibility of the needle projecting therefrom and accidentally injuring an unwary individual. It should be noted, that since the needle is returned within rigid housing 88, no additional cap is needed to cover the same. The advantage of this has been described hereinbefore.

In FIG. 4, there is shown another embodiment of the present invention. In FIG. 4, elements which are similar to those in FIGS. 1, 2 and 3 have been designated with the same numerals.

FIG. 4 shows the injector in an assembled condition wherein cartridge assembly 14 is engaged with power pack assembly 12. The injector in FIG. 4 operates in substantially the same manner as in the previous embodiment except that the cartridge assembly 14 is engaged with power pack assembly 12 with a conventional quarter turn attachment generally indicated at 150. In addition, rather than providing an operating rod 54 and pin 41, a single operating rod 152 is provided which includes a decreased diameter portion 154. Operating rod 152 operates to maintain balls 40 in an outwardly projected position from release pin assembly 156. The injector is provided with a rearward cap 158 which has a pocket clip 160 secured thereto. When cap 158 is removed, access to pushbutton 56 is made possible. When pushbutton 56 is manually actuated, compression spring member 64 is compressed and operating rod 152 is moved forwardly within release pin assembly 156 so that decreased diameter portion 154 is moved forwardly and permits balls 40 to retract therein. As a result, the forward end 164 (having an enlarged diameter) of sleeve 165 is permitted to ride over the withdrawn balls and, in cooperation with power spring 18, force rearwardly facing annular surface 168 of sleeve-like piston member 166 forwardly so that the forward end 170 of piston member 166 drives into plunger 94 to project the needle and then dispense medicament 90. After use, the cartridge assembly 14 can be disengaged from power pack assembly 12, at which time spring 114 operates to retract needle 96 into rigid outer covering 88 to provide the needle with a sanitary rigid outer covering for disposal.

In this embodiment, it can be appreciated that after an injection operation, the piston member 166 remains projecting from body 16 of power pack assembly 12 in a forward direction therefrom. In this embodiment, the engagement of cartridge assembly 14 with power pack assembly 12 does not accomplish the proper reloading of the power pack assembly. In other words, the engagement will not effectuate a recocking or compression of power spring 18. Rather, piston member 166 must be manually pushed back into body 16 by grasping the body with one hand and biasing the forward end of piston member 166 against a table or other rigid surface until the spring is held in a compressed position by balls 40.

It thus will be seen that the objects of this invention have been fully and effectively accomplished. It will be realized, however, that the foregoing preferred specific embodiments have been shown and described for the purpose of this invention and are subject to change without departure from such principles. Therefore, this invention includes all modifications encompassed with the spirit and scope of the following claims.

What is claimed is:

1. An automatic injector comprising:
   a reusable power pack assembly including a body and an energy releasing assembly carried by said body, said energy releasing assembly capable of providing multiple energy releasing strokes; and
   a disposable cartridge assembly adapted to be positioned in functionally cooperative relation with said power pack assembly to effectuate an injection operation therewith during one of said energy releasing strokes, said cartridge assembly comprising
   (i) a rigid housing,
   (ii) a container disposed within said rigid housing,
   (iii) a single charge of medicament normally contained within said container,
   (iv) a needle held in a normally protected position within said housing and adapted to communicate with said charge of medicament normally contained in said container, said needle being movable from said protected position within said housing to an unprotected projecting position from said housing in response to one of said energy releasing strokes,
   (v) a plunger disposed within said container and movable therethrough in response to one of said energy releasing strokes to force said medicament through said needle when said needle is moved into said unprotected projecting position from said housing, and
   (vi) a needle return spring constructed and arranged to move said needle from said unprotected projecting position to said protected position within said rigid housing,
   said disposable cartridge assembly being movable out of said functionally cooperative relation with said power pack assembly so that after said injection operation said cartridge assembly can be discarded as a separate unit from said power pack assembly with said rigid housing preventing unwanted contact with said needle disposed in said protected position therein, said energy releasing assembly carried by said body being maintained with said body after said injection operation for use with another cartridge assembly to effectuate another injection operation.

2. A reloadable automatic injector as claimed in claim 1, wherein said needle is mounted on a forward end of said container, and wherein said needle return spring moves said container rearwardly within said housing together with said needle after said disposable cartridge assembly is moved out of said functionally cooperative relation with said power pack assembly.

3. A reloadable automatic injector as claimed in claim 1, wherein said return spring is in a normally relaxed condition prior to said injection operation, said return spring receiving energy from said energy releasing assembly so as to become compressed during said one of said energy releasing strokes.

4. A reloadable automatic injector as claimed in claim 3, wherein said return spring decompresses, after being compressed during said one of said energy releasing strokes, to return said needle to said protected position within said housing.

5. A reloadable automatic injector as claimed in claim 4, wherein movement of said disposable cartridge assembly out of said functionally cooperative relation with said power pack assembly causes said return spring to decompress to return said needle to said protected position within said housing.

6. A reloadable automatic injector as claimed in claim 1, wherein said energy releasing assembly comprises an injection spring and a piston, said injection spring being operable to drive said piston forwardly through said container during said one of said energy releasing strokes.

7. A reloadable automatic injector as claimed in claim 6, wherein said piston engages and moves said plunger through said container during said one of said energy releasing strokes to enable said plunger to force said medicament through said needle.

8. A reloadable automatic injector as claimed in claim 6, wherein said injection spring is compressed prior to said one of said energy releasing strokes in response to said cartridge assembly being positioned in functionally cooperative relation with said power pack assembly.

9. A reloadable automatic injector as claimed in claim 6, wherein said injection spring operates to compress said return spring during said one of said energy releasing strokes, said return spring being decompressed as a result of the disengagement of said cartridge assembly with said power pack assembly to return said needle to said protected position within said housing.

10. A reloadable automatic injector as claimed in claim 1, wherein the charge of medicament is forwardly confined within said housing by a seal member which is conditionable to permit said medicament to enter a rearward end of said needle during said injection operation.

11. A reloadable automatic injector as claimed in claim 1, wherein said container is made from a glass material.

12. A method for performing successive injection operations comprising the steps of:
   performing a predetermined actuating procedure on a power pack assembly when said power pack assembly is in functionally cooperable relation with a cartridge assembly, said power pack assembly being capable of effectuating multiple injection operations;
   moving a needle from a protected position within a housing of said cartridge assembly to an unprotected projecting position in which the needle projects from the housing in response to said predetermined actuating procedure;
   dispensing a medicament through said needle;
   moving said power pack assembly out of said functionally cooperable relation with said cartridge assembly;
   returning said needle to said protected position within said housing; and
   moving said power pack assembly into said functionally cooperable relation with another cartridge assembly.

13. The method as claimed in claim 12, further comprising the step of compressing a power spring carried by said power pack assembly when said power pack assembly is moved into said functionally cooperable relation with said cartridge assembly.

14. The method according to claim 13, further comprising the step of releasing said power spring in response to said predetermined actuating procedure to effectuate one of said injection operations.

* * * * *